US011717665B2

(12) United States Patent
Kimball (10) Patent No.: US 11,717,665 B2
(45) Date of Patent: Aug. 8, 2023

(54) SYSTEM AND METHOD FOR EFFECTING NON-STANDARD FLUID LINE CONNECTIONS

(71) Applicant: Zoll Circulation, Inc., San Jose, CA (US)

(72) Inventor: David Searl Kimball, Irvine, CA (US)

(73) Assignee: Zoll Circulation, Inc., San Jose, CA (US)

( * ) Notice: Subject to any disclaimer, the term of this patent is extended or adjusted under 35 U.S.C. 154(b) by 0 days.

(21) Appl. No.: 15/483,851

(22) Filed: Apr. 10, 2017

(65) Prior Publication Data

US 2017/0333684 A1    Nov. 23, 2017

Related U.S. Application Data

(63) Continuation of application No. 11/804,459, filed on May 18, 2007, now Pat. No. 9,737,692.

(51) Int. Cl.
| | |
|---|---|
| *A61M 39/10* | (2006.01) |
| *A61M 5/44* | (2006.01) |
| *A61M 39/00* | (2006.01) |
| *A61M 5/14* | (2006.01) |
| *A61M 25/10* | (2013.01) |

(52) U.S. Cl.
CPC .............. *A61M 39/10* (2013.01); *A61M 5/44* (2013.01); *A61M 5/1408* (2013.01); *A61M 25/1011* (2013.01); *A61M 2039/0009* (2013.01); *A61M 2039/1033* (2013.01); *A61M 2039/1083* (2013.01); *A61M 2039/1088* (2013.01); *A61M 2039/1094* (2013.01)

(58) Field of Classification Search
CPC .......... A61M 39/10; A61M 2039/1027; A61M 2039/1033; A61M 2039/1083; A61M 2039/1088; A61M 2039/1094; A61M 5/44; F16L 37/24; F16L 37/2445; F16L 37/248; F16L 37/256
See application file for complete search history.

(56) References Cited

U.S. PATENT DOCUMENTS

| | | | | |
|---|---|---|---|---|
| 4,076,285 | A | * | 2/1978 | Martinez ............... F16L 37/252 285/332 |
| 4,824,145 | A | * | 4/1989 | Carlsson ................. F16L 37/12 285/38 |
| 5,207,640 | A | | 5/1993 | Hattler |
| 5,230,862 | A | | 7/1993 | Berry et al. |
| 5,271,743 | A | | 12/1993 | Hattler |

(Continued)

FOREIGN PATENT DOCUMENTS

| | | |
|---|---|---|
| JP | 09215754 | 8/1997 |
| WO | 2001083001 A1 | 11/2001 |
| WO | 2004037335 A1 | 5/2004 |

OTHER PUBLICATIONS

"Pointed". Dictionary.com. https://www.dictionary.com/browse/pointed. Accessed Mar. 5, 2019. (Year: 2019).*

(Continued)

*Primary Examiner* — Theodore J Stigell
(74) *Attorney, Agent, or Firm* — Fish & Richardson P.C.

(57) ABSTRACT

A Luer-like non-standard quick disconnect medical fluid connector that cannot be engaged with a standard Luer fitting.

20 Claims, 3 Drawing Sheets

(56) References Cited

U.S. PATENT DOCUMENTS

| | | | |
|---|---|---|---|
| 5,441,487 A * | 8/1995 | Vedder | A61M 39/045 604/167.03 |
| 5,450,516 A | 9/1995 | Pasquali et al. | |
| 5,470,659 A | 11/1995 | Baumgart et al. | |
| 5,725,949 A | 3/1998 | Pasquali et al. | |
| 5,735,809 A | 4/1998 | Gorsuch | |
| 5,735,826 A | 4/1998 | Richmond | |
| 5,755,690 A | 5/1998 | Saab | |
| 5,837,003 A | 11/1998 | Ginsburg | |
| 5,876,667 A | 3/1999 | Gremel et al. | |
| 5,879,329 A | 3/1999 | Ginsburg | |
| 5,989,238 A | 11/1999 | Ginsburg | |
| 6,004,289 A | 12/1999 | Saab | |
| 6,019,783 A | 2/2000 | Philips et al. | |
| 6,042,559 A | 3/2000 | Dobak | |
| 6,096,068 A | 8/2000 | Dobak et al. | |
| 6,110,168 A | 8/2000 | Ginsburg | |
| 6,126,684 A | 10/2000 | Gobin et al. | |
| 6,146,411 A | 11/2000 | Noda et al. | |
| 6,149,670 A | 11/2000 | Worthen et al. | |
| 6,149,673 A | 11/2000 | Ginsburg | |
| 6,149,676 A | 11/2000 | Ginsburg | |
| 6,149,677 A | 11/2000 | Dobak | |
| 6,165,207 A | 12/2000 | Balding et al. | |
| 6,224,624 B1 | 5/2001 | Lasheras et al. | |
| 6,231,594 B1 | 5/2001 | Dae | |
| 6,231,595 B1 | 5/2001 | Dobak | |
| 6,235,048 B1 | 5/2001 | Dobak | |
| 6,238,428 B1 | 5/2001 | Werneth et al. | |
| 6,245,095 B1 | 6/2001 | Dobak et al. | |
| 6,251,129 B1 | 6/2001 | Dobak et al. | |
| 6,251,130 B1 | 6/2001 | Dobak et al. | |
| 6,254,626 B1 | 7/2001 | Dobak et al. | |
| 6,261,312 B1 | 7/2001 | Dobak | |
| 6,264,679 B1 | 7/2001 | Keller et al. | |
| 6,287,326 B1 | 9/2001 | Pecor | |
| 6,290,717 B1 | 9/2001 | Philips | |
| 6,299,599 B1 | 10/2001 | Pham et al. | |
| 6,306,161 B1 | 10/2001 | Ginsburg | |
| 6,312,452 B1 | 11/2001 | Dobak et al. | |
| 6,325,818 B1 | 12/2001 | Werneth | |
| 6,338,727 B1 | 1/2002 | Noda et al. | |
| 6,364,899 B1 | 4/2002 | Dobak | |
| 6,368,304 B1 | 4/2002 | Aliberto et al. | |
| 6,379,378 B1 | 4/2002 | Werneth et al. | |
| 6,383,210 B1 | 5/2002 | Magers et al. | |
| 6,393,320 B2 | 5/2002 | Lasersohn et al. | |
| 6,405,080 B1 | 6/2002 | Lasersohn et al. | |
| 6,409,747 B1 | 6/2002 | Gobin et al. | |
| 6,416,533 B1 | 7/2002 | Gobin et al. | |
| 6,419,643 B1 | 7/2002 | Shimada et al. | |
| 6,428,563 B1 | 8/2002 | Keller | |
| 6,432,124 B1 | 8/2002 | Worthen et al. | |
| 6,436,130 B1 | 8/2002 | Philips et al. | |
| 6,436,131 B1 | 8/2002 | Ginsburg | |
| 6,440,158 B1 | 8/2002 | Saab | |
| 6,447,474 B1 | 9/2002 | Balding | |
| 6,450,987 B1 | 9/2002 | Kramer | |
| 6,450,990 B1 | 9/2002 | Walker et al. | |
| 6,451,045 B1 | 9/2002 | Walker et al. | |
| 6,454,792 B1 | 9/2002 | Noda et al. | |
| 6,454,793 B1 | 9/2002 | Evans et al. | |
| 6,458,150 B1 | 10/2002 | Evans et al. | |
| 6,460,544 B1 | 10/2002 | Worthen | |
| 6,464,716 B1 | 10/2002 | Dobak et al. | |
| 6,468,296 B1 | 10/2002 | Dobak et al. | |
| 6,471,717 B1 | 10/2002 | Dobak et al. | |
| 6,475,231 B2 | 11/2002 | Dobak et al. | |
| 6,478,811 B1 | 11/2002 | Dobak et al. | |
| 6,478,812 B2 | 11/2002 | Dobak et al. | |
| 6,482,226 B1 | 11/2002 | Dobak | |
| 6,491,039 B1 | 12/2002 | Dobak | |
| 6,491,716 B2 | 12/2002 | Dobak et al. | |
| 6,494,903 B2 | 12/2002 | Pecor | |
| 6,497,721 B2 | 12/2002 | Robert et al. | |
| 6,516,224 B2 | 2/2003 | Lasersohn et al. | |
| 6,520,933 B1 | 2/2003 | Evans et al. | |
| 6,527,798 B2 | 3/2003 | Ginsburg et al. | |
| 6,529,775 B2 | 3/2003 | Whitebook et al. | |
| 6,530,946 B1 | 3/2003 | Noda et al. | |
| 6,533,804 B2 | 3/2003 | Dobak et al. | |
| 6,540,771 B2 | 4/2003 | Dobak et al. | |
| 6,544,282 B1 | 4/2003 | Dae et al. | |
| 6,551,349 B2 | 4/2003 | Lasheras et al. | |
| 6,554,797 B1 | 4/2003 | Worthen | |
| 6,558,412 B2 | 5/2003 | Dobak | |
| 6,572,538 B2 | 6/2003 | Takase | |
| 6,572,638 B1 | 6/2003 | Dae et al. | |
| 6,572,640 B1 | 6/2003 | Balding et al. | |
| 6,576,001 B2 | 6/2003 | Werneth et al. | |
| 6,576,002 B2 | 6/2003 | Dobak | |
| 6,581,403 B2 | 6/2003 | Whitebook et al. | |
| 6,582,398 B1 | 6/2003 | Worthen et al. | |
| 6,582,455 B1 | 6/2003 | Dobak et al. | |
| 6,582,457 B2 | 6/2003 | Dae et al. | |
| 6,585,692 B1 | 7/2003 | Worthen | |
| 6,585,752 B2 | 7/2003 | Dobak et al. | |
| 6,589,271 B1 | 7/2003 | Tzeng et al. | |
| 6,595,967 B2 | 7/2003 | Kramer | |
| 6,599,312 B2 | 7/2003 | Dobak | |
| 6,602,243 B2 | 8/2003 | Noda | |
| 6,602,276 B2 | 8/2003 | Dobak et al. | |
| 6,607,517 B1 | 8/2003 | Dae et al. | |
| 6,610,083 B2 | 8/2003 | Keller et al. | |
| 6,620,130 B1 | 9/2003 | Ginsburg | |
| 6,620,131 B2 | 9/2003 | Pham et al. | |
| 6,620,188 B1 | 9/2003 | Robert et al. | |
| 6,620,189 B1 | 9/2003 | Machold et al. | |
| 6,623,516 B2 | 9/2003 | Saab | |
| 6,635,076 B1 | 10/2003 | Ginsburg | |
| 6,641,602 B2 | 11/2003 | Balding | |
| 6,641,603 B2 | 11/2003 | Walker et al. | |
| 6,645,234 B2 | 11/2003 | Evans et al. | |
| 6,648,906 B2 | 11/2003 | Lasheras et al. | |
| 6,648,908 B2 | 11/2003 | Dobak et al. | |
| 6,652,565 B1 | 11/2003 | Shimada et al. | |
| 6,656,209 B1 | 12/2003 | Ginsburg | |
| 6,660,028 B2 | 12/2003 | Magers et al. | |
| 6,673,098 B1 | 1/2004 | Machold et al. | |
| 6,676,688 B2 | 1/2004 | Dobak et al. | |
| 6,676,689 B2 | 1/2004 | Dobak et al. | |
| 6,676,690 B2 | 1/2004 | Werneth | |
| 6,679,906 B2 | 1/2004 | Hammack et al. | |
| 6,679,907 B2 | 1/2004 | Dobak et al. | |
| 6,682,551 B1 | 1/2004 | Worthen et al. | |
| 6,685,732 B2 | 2/2004 | Kramer | |
| 6,685,733 B1 | 2/2004 | Dae et al. | |
| 6,692,488 B2 | 2/2004 | Dobak et al. | |
| 6,692,519 B1 | 2/2004 | Hayes | |
| 6,695,873 B2 | 2/2004 | Dobak et al. | |
| 6,695,874 B2 | 2/2004 | Machold et al. | |
| 6,699,268 B2 | 3/2004 | Kordis et al. | |
| 6,702,783 B1 | 3/2004 | Dae et al. | |
| 6,702,839 B1 | 3/2004 | Dae et al. | |
| 6,702,840 B2 | 3/2004 | Keller et al. | |
| 6,702,841 B2 | 3/2004 | Nest et al. | |
| 6,702,842 B2 | 3/2004 | Dobak et al. | |
| 6,706,060 B2 | 3/2004 | Tzeng et al. | |
| 6,709,448 B2 | 3/2004 | Walker et al. | |
| 6,716,188 B2 | 4/2004 | Noda et al. | |
| 6,716,236 B1 | 4/2004 | Tzeng et al. | |
| 6,719,723 B2 | 4/2004 | Werneth | |
| 6,719,724 B1 | 4/2004 | Walker et al. | |
| 6,719,779 B2 | 4/2004 | Daoud | |
| 6,726,653 B2 | 4/2004 | Noda et al. | |
| 6,726,708 B2 | 4/2004 | Lasheras | |
| 6,726,710 B2 | 4/2004 | Worthen et al. | |
| 6,730,059 B2 | 5/2004 | Caizza et al. | |
| 6,733,517 B1 | 5/2004 | Collins | |
| 6,740,109 B2 | 5/2004 | Dobak | |
| 6,749,585 B2 | 6/2004 | Aliberto et al. | |
| 6,749,625 B2 | 6/2004 | Pompa et al. | |
| 6,752,786 B2 | 6/2004 | Callister | |
| 6,755,850 B2 | 6/2004 | Dobak | |

(56) References Cited

U.S. PATENT DOCUMENTS

| | | |
|---|---|---|
| 6,755,851 B2 | 6/2004 | Noda et al. |
| 6,796,995 B2 | 9/2004 | Pompa |
| 6,964,406 B2 | 11/2005 | Doyle |
| 2001/0007951 A1 | 7/2001 | Dobak |
| 2001/0016764 A1 | 8/2001 | Dobak |
| 2001/0041923 A1 | 11/2001 | Dobak |
| 2002/0007203 A1 | 1/2002 | Gilmartin et al. |
| 2002/0016621 A1 | 2/2002 | Werneth et al. |
| 2002/0068964 A1 | 6/2002 | Dobak |
| 2002/0077680 A1 | 6/2002 | Noda |
| 2002/0091429 A1 | 7/2002 | Dobak et al. |
| 2002/0111616 A1 | 8/2002 | Dea et al. |
| 2002/0116039 A1 | 8/2002 | Walker et al. |
| 2002/0151946 A1 | 10/2002 | Dobak |
| 2002/0177804 A1 | 11/2002 | Saab |
| 2002/0183692 A1 | 12/2002 | Callister |
| 2002/0193738 A1 | 12/2002 | Adzich et al. |
| 2002/0193853 A1 | 12/2002 | Worthen et al. |
| 2002/0193854 A1 | 12/2002 | Dobak et al. |
| 2003/0078641 A1 | 4/2003 | Dobak |
| 2003/0114835 A1 | 6/2003 | Noda |
| 2003/0144714 A1 | 7/2003 | Dobak |
| 2003/0187489 A1 | 10/2003 | Dobak et al. |
| 2003/0195465 A1 | 10/2003 | Worthen |
| 2003/0195466 A1 | 10/2003 | Pham et al. |
| 2003/0195597 A1 | 10/2003 | Keller et al. |
| 2003/0216799 A1 | 11/2003 | Worthen et al. |
| 2003/0225336 A1 | 12/2003 | Callister et al. |
| 2004/0034399 A1 | 2/2004 | Ginsburg |
| 2004/0039431 A1 | 2/2004 | Machold et al. |
| 2004/0044388 A1 | 3/2004 | Pham et al. |
| 2004/0050154 A1 | 3/2004 | Machold et al. |
| 2004/0054325 A1 | 3/2004 | Ginsburg |
| 2004/0073280 A1 | 4/2004 | Dae et al. |
| 2004/0087934 A1 | 5/2004 | Dobak et al. |
| 2004/0102825 A1 | 5/2004 | Daoud |
| 2004/0102826 A1 | 5/2004 | Lasheras et al. |
| 2004/0102827 A1 | 5/2004 | Werneth |
| 2004/0106969 A1 | 6/2004 | Dobak et al. |
| 2004/0111138 A1 | 6/2004 | Bleam et al. |
| 2004/0116987 A1 | 6/2004 | Magers et al. |
| 2004/0116988 A1 | 6/2004 | Hammack et al. |
| 2004/0127851 A1 | 7/2004 | Noda et al. |
| 2004/0201216 A1 | 10/2004 | Segal et al. |
| 2004/0215297 A1* | 10/2004 | Collins .............. A61F 7/12 607/105 |
| 2007/0076401 A1* | 4/2007 | Carrez .............. A61M 39/10 361/816 |
| 2007/0158294 A1* | 7/2007 | Tanaka .............. B65D 1/0223 215/43 |

OTHER PUBLICATIONS

U.S. Appl. No. 60/272,442, Worthen et al.

* cited by examiner

Fig.1

SYSTEM AND METHOD FOR EFFECTING NON-STANDARD FLUID LINE CONNECTIONS

FIELD

The present invention relates generally to systems and methods for effecting non-standard fluid line connections.

BACKGROUND

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons such as keeping patients warm during skin graft surgery. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

As critically recognized herein, a need exists to effect fluid line connections in medical devices such as the catheters described above to avoid unintentionally connecting a component such as a syringe having a standard connector such as a standard Luer fitting with a connector leading to a lumen that is not intended to receive the fluid in the component.

SUMMARY OF THE INVENTION

A medical fluid connector system includes a unitary male connector body defining an inner hollow male cone and an outer annular sleeve surrounding the male cone and radially spaced from the cone. The sleeve is internally threaded and the male cone extends axially beyond the sleeve. The body includes structure that prevents engaging a standard female Luer fitting with the body.

The structure which prevents engagement with a standard female Luer can include an outer diameter of the male cone that is greater than an outer diameter of a male cone of a standard male Luer fitting. In addition or alternatively, the structure can include an inner diameter of the sleeve that is greater than an inner diameter of a sleeve of a standard male Luer fitting. Yet again, in addition or as an alternative the structure may include a thread pitch of the sleeve that is greater than a thread pitch of a sleeve of a standard male Luer fitting.

A unitary female connector body may also provided which defines a female cone having an external radially elongated triangular thread configured for engaging the threads of the sleeve.

In another aspect, a medical fluid connector system includes a unitary female connector body defining a female cone having an external radially elongated triangular thread configured for engaging threads of a sleeve of a male connector body.

In still another aspect, a method includes providing a male connector having a central hollow male cone spaced from an annular surrounding internally threaded sleeve. The method further includes providing a female connector having a female cone with a radially elongated triangular-shaped thread configured for engaging the sleeve. The male connector is unable to receive a standard female Luer fitting and the female connector is unable to engage a standard male Luer fitting.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
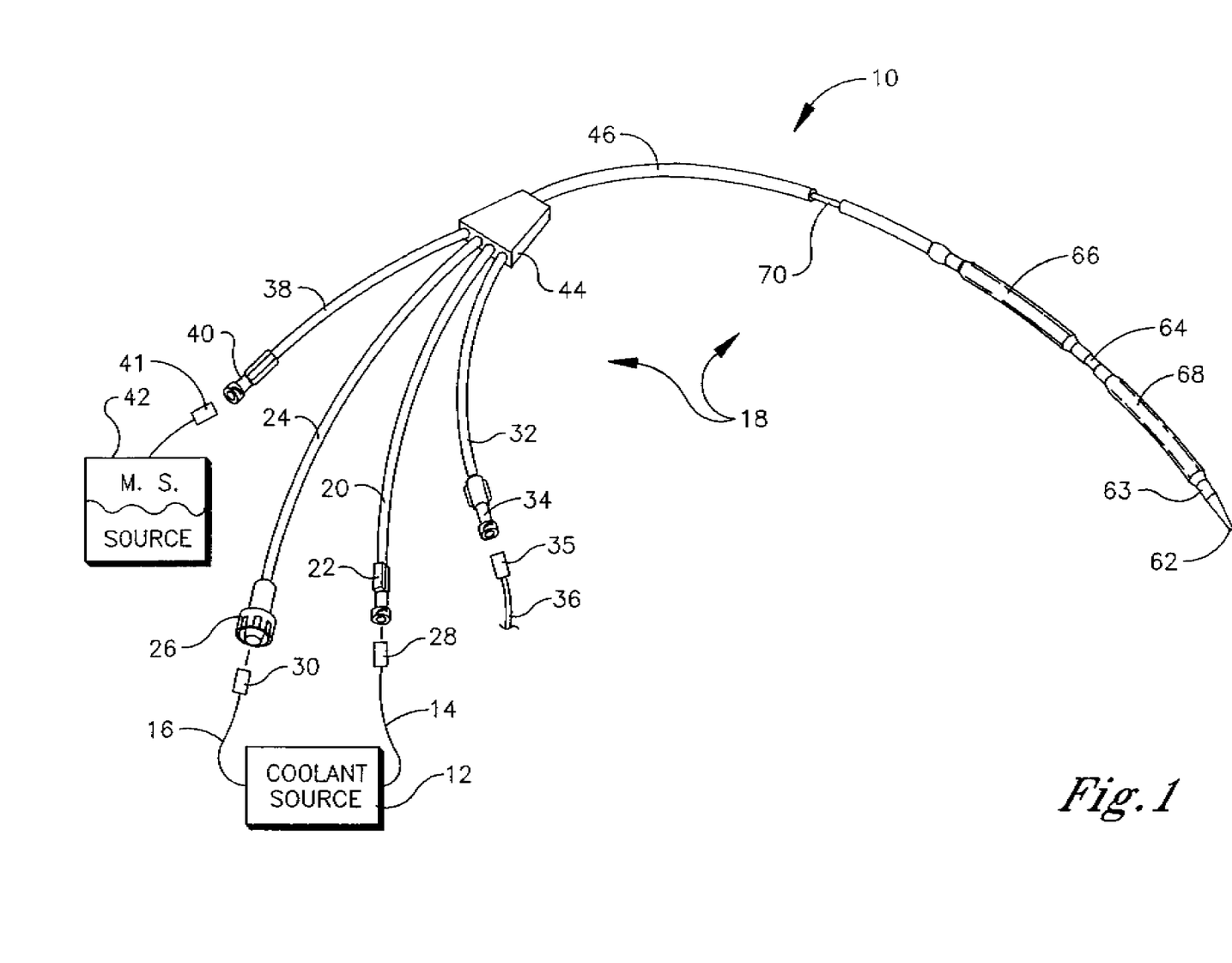
FIG. 1 is a perspective view of a non-limiting intravascular heat exchange catheter, schematically showing a medicament source and heat exchange fluid source in an exploded relationship with the catheter.

Referring initially to FIG. 1, a therapeutic catheter system, generally designated 10, is shown for establishing and maintaining hypothermia in a patient, or for attenuating a fever spike in a patient and then maintaining normal body temperature in the patient. The catheter can also be used to maintain a patient's temperature during surgery.

While FIG. 1 shows an exemplary embodiment of one heat exchange catheter, it is to be understood that the present invention applies to any of the catheters and accompanying heat exchange controllers disclosed in the above-referenced patents, including but not limited to the helical shaped devices disclosed in Alsius' U.S. Pat. Nos. 6,451,045 and 6,520,933. Also, one of the spiral-shaped or convoluted-shaped catheters disclosed in Alsius' U.S. Pat. Nos. 6,749,625 and 6,796,995, both of which are incorporated herein by reference, can be used.

It is to be further understood that while the novel fluid connectors shown and described herein are illustrated in an intravascular temperature control catheter application, they can be used in other medical devices as well.

Commencing the description of the system 10 at the proximal end, as shown the exemplary non-limiting system 10 includes a heat exchange fluid source 12 that can be a water-bath heat exchange system or a TEC-based heat exchange system such as any of the systems disclosed in one or more of the above-referenced patents. Or, the source 12 can be a source of compressed gas. In any case, the heat exchange fluid source provides warmed or cooled heat exchange fluid such as saline or compressed gas through a heat exchange fluid supply line 14, and heat exchange fluid is returned to the source 12 via a heat exchange fluid return line 16. A catheter, generally designated 18, includes a source tube 20 terminating in a female fitting 22, described further below. Also, the catheter 18 has a return tube 24 terminating in a male fitting 26, also described further below. The fittings 22, 26 can be selectively engaged with complementary fittings 28, 30 (shown schematically in FIG. 1) of the lines 14, 16 and also described further below to establish a closed circuit heat exchange fluid path between the catheter 18 and heat exchange fluid source 12. As intended herein, the fittings 22, 26, 28, 30 are quick disconnect fittings that cannot be engaged with standard Luer fittings, to avoid incorrect connections.

With more specificity, a non-limiting catheter 18 may include a guide wire and primary infusion tube 32 that terminates in a fitting such as a standard female Luer 34. A standard male Luer 35 (shown schematically in FIG. 1) can be engaged with the female Luer 34 to advance a guide wire 36 through the tube 32 in accordance with central venous catheter placement principles, or medicament or other fluid can be infused through the guide wire and primary infusion tube 32 by means of the standard Luers 34, 35.

Moreover, a secondary infusion tube 38 with standard female Luer fitting 40 can be selectively engaged with a standard male Luer fitting 41 (shown schematically in FIG. 1) of a medicament source 42 for infusing fluid from the source 42 through the secondary tube 38.

The source 42 may be an IV bag. Or, the source 42 may be a syringe. In any case, because the coolant line fittings 22, 26, 28, 30 cannot be engaged with standard Luers, the coolant in the source 12 cannot be erroneously connected to the infusion lines 32, 38. Likewise, for the same reason the source 42 such as a syringe cannot be erroneously engaged with the coolant lines 20, 24.

By "standard Luer" is meant a quick disconnect component, typically hard plastic, which in its male implementation has an inner cone surrounded by an outer internally threaded sleeve spaced from the cone, with the diameter at the tip of the cone being about 3.93 mm, a minimum internal thread diameter of the sleeve being about 7.00 mm, and a thread pitch being about 1.20 mm. In its female implementation a "standard Luer" is a female cone with external stub-like protrusions that act as threads and that are sized and shaped for engaging the internally threaded sleeve of the standard male Luer described above.

The tubes 20, 24, 32, 38 may be held in a distally-tapered connector manifold 44. The connector manifold 44 establishes respective pathways for fluid communication between the tubes 20, 24, 32, 38 and respective lumens in a catheter body 46.

In any case, the connector manifold 44 establishes a pathway for fluid communication between the heat exchange fluid supply tube 20 and the heat exchange fluid supply lumen of the catheter. Likewise, the connector manifold 44 establishes a pathway for fluid communication between the heat exchange fluid return tube 24 and the heat exchange fluid return lumen. Further, the connector manifold 44 establishes a pathway for fluid communication between the guide wire and primary infusion tube 32, and the guide wire lumen, which can terminate at an open distal hole 62 defined by a distally tapered and chamfered distal tip 63 of the catheter body 46. Also, the connector manifold 44 establishes a pathway for fluid communication between the secondary infusion tube 38 and the secondary infusion lumen, which can terminate at an infusion port 64 in a distal segment of the catheter body 46. Additional ports can be provided along the length of the catheter.

An exemplary non-limiting catheter 18 has a distally-located heat exchange member for effecting heat exchange with the patient when the catheter is positioned in the vasculature or rectum or other orifice of a patient. The heat exchange member can be any of the heat exchange members disclosed in the above-referenced patents. By way of example, a non-limiting catheter shown in FIG. 1 can have proximal and distal thin-walled heat exchange membranes 66, 68 that are arranged along the last fifteen or so centimeters of the catheter body 46 and that are bonded to the outer surface of the catheter body 46, with the infusion port 64 being located between the heat exchange membranes 66, 68. Thus, each preferred non-limiting heat exchange membrane is about six centimeters to seven and one-half centimeters in length, with the heat exchange membranes being longitudinally spaced from each other along the catheter body 46 in the preferred embodiment shown. Essentially, the heat exchange membranes 66, 68 extend along most or all of that portion of the catheter 46 that is intubated within the patient. The heat exchange membranes can be established by a medical balloon material.

The heat exchange membranes 66, 68 can be inflated with heat exchange fluid from the heat exchange fluid source 12 as supplied from the heat exchange fluid supply lumen, and heat exchange fluid from the heat exchange membranes 66, 68 is returned via the heat exchange fluid return lumen to the heat exchange fluid source 12.

If desired, a temperature sensor 70 such as a thermistor or other suitable device can be attached to the catheter 18 as shown. The sensor 70 can be mounted on the catheter 18 by solvent bonding at a point that is proximal to the membranes 66, 68. Or, the sensor 70 can be disposed in a lumen of the catheter 18, or attached to a wire that is disposed in a lumen of the catheter 18, with the sensor hanging outside the catheter 18. Alternatively, a separate temperature probe can be used, such as the esophageal probe disclosed in U.S. Pat. No. 6,290,717, incorporated herein by reference. As yet another alternative, a rectal probe or tympanic temperature sensor can be used. In any case, the sensor is electrically connected to the heat exchange fluid source 12 for control of the temperature of the heat exchange fluid as described in various of the above-referenced patents.

As envisioned by the present invention, the structure set forth above can be used in many medical applications to cool a patient and/or to maintain temperature in a normothermic or hypothermic patient, for purposes of improving the medical outcomes of, e.g., cardiac arrest patients, patients suffering from myocardial infarction or stroke, etc. As another example, head trauma can be treated by and after lowering and maintaining the patient's temperature below normal body temperature. Preferably, particularly in the case of myocardial infarction, the heat exchange portions are advanced into the vena cava of the patient to cool blood flowing to the heart. The catheter can be used to keep patients warm during skin graft surgery or other surgery.

Figure 2:
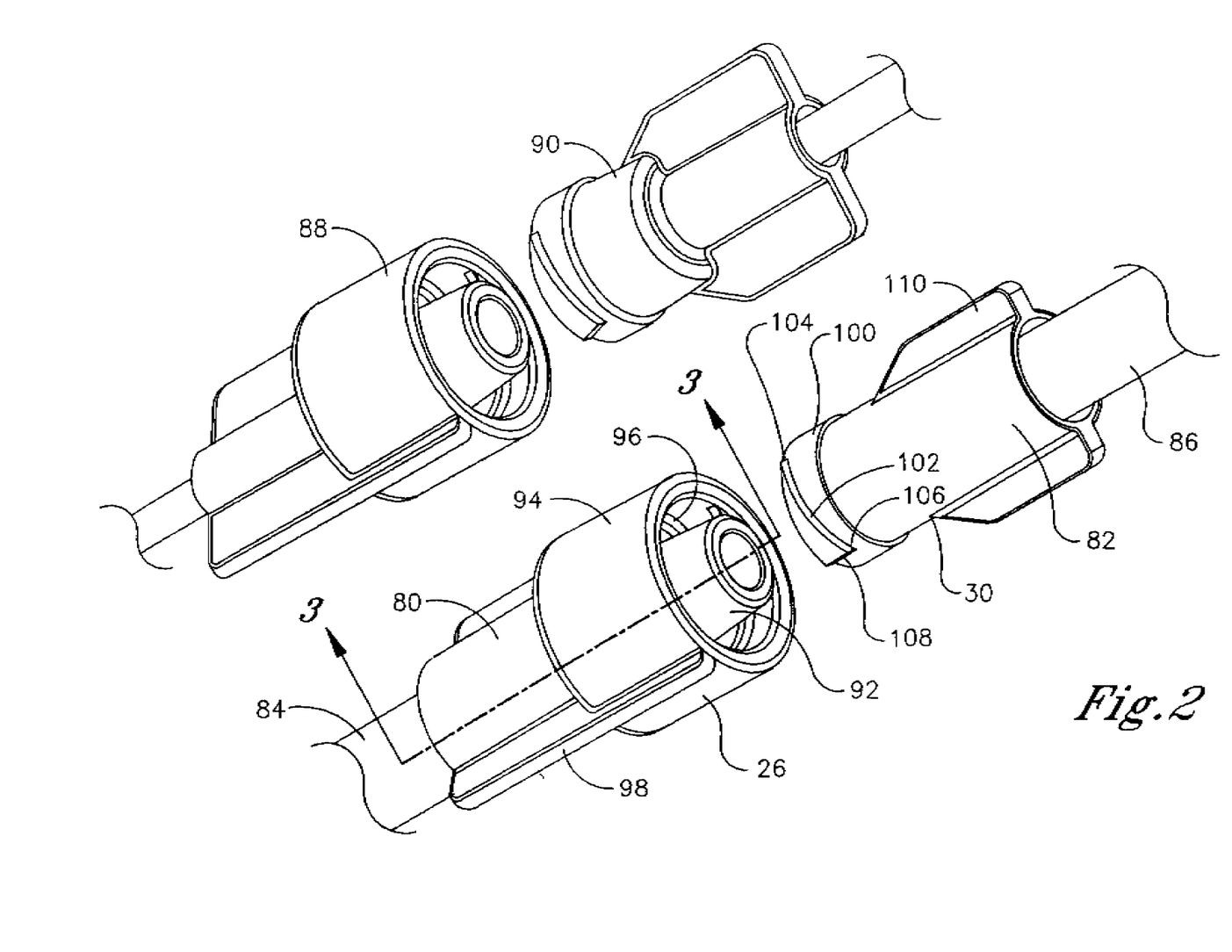
FIG. 2 is a perspective view showing two sets of male and female connectors in accordance with present principles.
Figure 3:
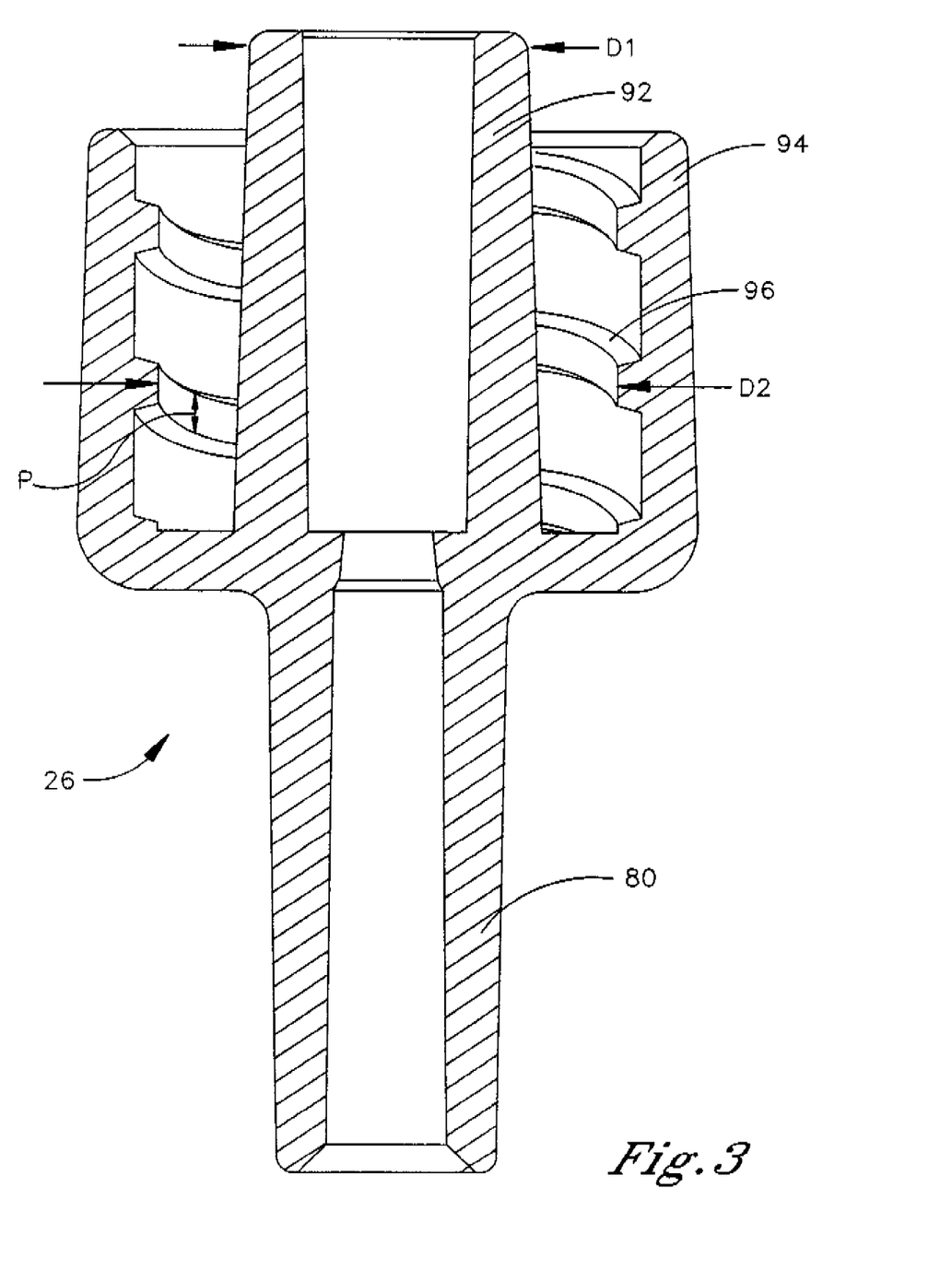
FIG. 3 is a cross-sectional diagram as seen along the line 3-3 in FIG. 2.

Now referring to FIGS. 2 and 3, details of the present connectors, male and female, can be seen. FIG. 2 shows the male and female connectors 26, 30 described above with relatively large tube barrels 80, 82 for accepting relatively large tubes 84, 86, respectively. Also shown are male and female connectors 88, 90 that in all essential respects are identical to the other connectors 26, 30 except they have smaller tube barrels for accepting smaller tubes. Accordingly, with that difference in mind discussion will focus on the first set of connectors 26, 30.

The male connector includes an inner hollow cone 92 that protrudes slightly beyond an outer annular sleeve 94 as shown. While referred to for simplicity as a "cone", as can be seen from the drawing the cone 92 technically is frusto-conical. The cone 92 is spaced from the sleeve 94 so that the female connector 30 can be advanced between the sleeve 94 and cone 92 as will be described shortly. To this end, the interior of the sleeve 94 is formed with threads 96, preferably two-start threads. The sleeve 94 joins with the tube barrel 80 as shown, and gripping flanges 98 are formed lengthwise along the tube barrel 80 and sleeve 94 to assist a person in grasping and rotating the connector 26.

Turning to the female connector 30, the tube barrel 82 is hollow and frusto-conical, terminating in a ring-shaped end flange 100 that extends radially beyond the tube barrel 82 as shown. On the exterior of the flange 100, at least one and preferably radially diametrically opposed radially elongated male threads 102 are formed. In the preferred implementation a male thread 102 has a generally triangular shape; accordingly, one end 104 of the thread 102 is substantially pointed, with the male thread 102 flaring out in the axial dimension as it extends radially around the flange 100 to an opposed broad end 106 having a flat axially-oriented base 108 as shown. Like the male connector 26, the female connector 30 is formed with gripping flanges 110 that are formed lengthwise along the tube barrel 82 to assist a person in grasping and rotating the connector 30.

With the above structure, the female connector 30 can be advanced between the sleeve 94 and cone 92 of the male connector 26 while rotating the connectors 26, 30 relative to each other to engage them in an interference fit.

While the connectors 26, 30 may be engaged with each other, they may not be engaged with complementary standard Luer fittings owing in part to the structure above, e.g., the radially elongated male thread 102. Also preventing engagement of the connectors 26, 30 with standard Luer fittings are the preferred sizes and thread geometries set forth below.

Specifically and referring to FIG. 3, the outer diameter "D1" of the cone 92 at its open end is about 5.97 mm, whereas recall that the diameter at the tip of the cone of a standard male Luer is about 3.93 mm, meaning that the cone 92 of the male connector 26 shown in FIGS. 2 and 3 is too large to allow a standard female Luer to slide over it. Furthermore, the minimum internal thread diameter "D2" of the sleeve 94 is about 9.68 mm, whereas recall that the minimum internal thread diameter of the sleeve of a standard male Luer is about 7.00 mm, meaning that the male stubs of a standard female Luer could not extend radially far enough to reach the threads 96 of the male connector 26. Still further, the thread pitch "P" of the male connector 26 is about 3.45 mm compared to the standard pitch of about 1.20 mm.

The connectors described herein may be unitary molded structures made of a plastic such as nylon, polypropylene, polyethylene, or other suitable medical plastic.

While the particular SYSTEM AND METHOD FOR EFFECTING NON-STANDARD FLUID LINE CONNECTIONS is herein shown and described in detail, it is to be understood that the subject matter which is encompassed by the present invention is limited only by the claims.

What is claimed is:

1. A medical fluid connector system comprising:
a catheter;
a female connector body; and
a heat exchange fluid tube connected to the catheter, the heat exchange fluid tube terminating at the female connector body configured to engage with a corresponding male connector of a heat exchange fluid source;
the female connector body defining:
a tube receptacle having a first end; and
an end flange on the first end and extending radially beyond the tube receptacle, the end flange defining an exterior, at least one thread being formed on the exterior of the end flange, the at least one thread being radially elongated to prevent a standard male Luer fitting from interfacing with the female connector body by blocking a sleeve thread of the standard male Luer fitting, the at least one thread being configured to allow the end flange to advance between a sleeve and a cone of the corresponding male connector, the at least one thread having an elongated triangular shape along an edge of the end flange, wherein an end of the at least one thread is substantially pointed, and wherein the substantially pointed end of the at least one thread is positioned at the edge of the end flange, the at least one thread being configured to engage the sleeve of the corresponding male connector in an interference fit;
wherein the sleeve of the corresponding male connector has an inner diameter that is larger than an inner diameter of a sleeve of the standard male Luer fitting and includes a sleeve thread configured to interface with the at least one thread of the end flange of the female connector body.

2. The medical fluid connector system of claim 1, wherein the at least one thread is a first thread and the system comprises at least a second thread formed on the exterior of the end flange.

3. The medical fluid connector system of claim 1, wherein the at least one thread flares out as it extends radially around the end flange.

4. The medical fluid connector system of claim 1, wherein the at least one thread defines a second end that defines a flat axially-oriented base.

5. The medical fluid connector system of claim 1, wherein the female connector body comprises at least a first gripping flange extending lengthwise along the female connector body and extending radially past the end flange.

6. The medical fluid connector system of claim 1, wherein the at least one thread is sized to interface with the sleeve thread having the inner diameter less than or equal to 9.68 millimeters and larger than the inner diameter of the sleeve of the standard male Luer fitting.

7. The medical fluid connector system of claim 1, wherein the at least one thread is sized to interface with the sleeve thread having a thread pitch less than or equal to 3.45 millimeters and greater than a thread pitch of the standard male Luer fitting.

8. The medical fluid connector system of claim 1, wherein a diameter of a tip of the cone of the corresponding male connector is less than or equal to 5.97 millimeters and greater than another diameter at a tip of a cone of the standard male Luer fitting.

9. The medical fluid connector system of claim 1, wherein the at least one thread extends radially around the end flange to an opposed broad end having a flat axially-oriented base.

10. A medical fluid connector system comprising:
a catheter;
a female connector body; and a heat exchange fluid tube connected to the catheter, the heat exchange fluid tube terminating at the female connector body configured to engage with a corresponding male connector of a heat exchange fluid source;
the female connector body defining:
an end flange;
a tube barrel having a first end at the end flange; and
a thread being coupled to the first end of the tube barrel, the thread having an elongated triangular shape along an edge of the end flange, wherein an end of the thread is substantially pointed, and wherein the substantially pointed end of the thread is positioned at the edge of the end flange, wherein the thread prevents a standard male Luer fitting from interfacing with the female connector body by blocking a sleeve thread of the standard male Luer fitting, the thread being configured to allow the tube barrel to advance between a sleeve and a cone of the corresponding male connector in an interference fit;
wherein the sleeve of the corresponding male connector has an inner diameter that is larger than an inner diameter of a sleeve of the standard male Luer fitting and includes a sleeve thread configured to interface with the thread of the female connector body.

11. The medical fluid connector system of claim 10, wherein the end flange is a ring-shaped end flange on the first end of the tube barrel and extends radially beyond the tube barrel, the thread being formed on the ring-shaped end flange.

12. The medical fluid connector system of claim 10, wherein the thread is a first thread and the system comprises at least a second thread coupled to the first end of the tube barrel.

13. The medical fluid connector system of claim 10, wherein the thread flares out as it extends radially around the end flange.

14. The medical fluid connector system of claim 10, wherein a second end of the thread defines a flat axially-oriented base.

15. The medical fluid connector system of claim 10, wherein the female connector body comprises at least a first gripping flange extending lengthwise along the female connector body and extending radially past the end flange.

16. A medical fluid connector system comprising:
a catheter;
a female connector body;
a heat exchange fluid tube connected to the catheter, the heat exchange fluid tube terminating at the female connector body configured to engage with a corresponding male connector of a heat exchange fluid source;
the female connector body defining:
a tube barrel having a first end defined by an end flange; and
a thread being coupled to the first end of the tube barrel, the thread having an elongated triangular shape along an edge of the end flange, wherein an end of the thread is substantially pointed, and wherein the substantially pointed end of the thread is positioned at the edge of the end flange, wherein the thread prevents a standard male Luer fitting from interfacing with the female connector body by blocking a sleeve thread of the standard male Luer fitting,
wherein the sleeve of the corresponding male connector has an inner diameter that is larger than an inner diameter of a sleeve of the standard male Luer fitting and includes a sleeve thread configured to interface with the thread.

17. The medical fluid connector system of claim 16, wherein the end flange is a ring-shaped end flange on the first end of the tube barrel and extends radially beyond the tube barrel, the thread being formed on the ring-shaped end flange.

18. The medical fluid connector system of claim 16, wherein the thread is a first thread and the system comprises at least a second thread coupled to the first end of the tube barrel.

19. The medical fluid connector system of claim 16, wherein the thread flares out as it extends radially around the end flange.

20. The medical fluid connector system of claim 16, wherein the female body comprises at least a first gripping flange extending lengthwise along the female connector body and extending radially past the end flange.

* * * * *

UNITED STATES PATENT AND TRADEMARK OFFICE
CERTIFICATE OF CORRECTION

| | | |
|---|---|---|
| PATENT NO. | : 11,717,665 B2 | Page 1 of 1 |
| APPLICATION NO. | : 15/483851 | |
| DATED | : August 8, 2023 | |
| INVENTOR(S) | : David Searl Kimball | |

It is certified that error appears in the above-identified patent and that said Letters Patent is hereby corrected as shown below:

In the Specification

Column 1, Line 5, insert:
--CROSS REFERENCE
The present application is a continuation of application number 11/804,459, filed May 18, 2007 and issued as patent number 9,737,692 on August 22, 2017 in the United States, and is hereby incorporated by reference.--

Signed and Sealed this
Twenty-seventh Day of February, 2024

Katherine Kelly Vidal
*Director of the United States Patent and Trademark Office*